United States Patent [19]

Kletschka

[11] Patent Number: 4,794,928
[45] Date of Patent: Jan. 3, 1989

[54] ANGIOPLASTY DEVICE AND METHOD OF USING THE SAME

[76] Inventor: Harold D. Kletschka, 1925 Noble Dr., Minneapolis, Minn. 55422

[21] Appl. No.: 61,104

[22] Filed: Jun. 10, 1987

[51] Int. Cl.$^4$ .......................................... A61M 29/02
[52] U.S. Cl. .................................... 128/344; 128/305; 128/348.1; 128/303.1; 604/22; 604/101
[58] Field of Search .................. 128/344, 348.1, 305, 128/303.1; 604/101, 22, 96

[56] References Cited

U.S. PATENT DOCUMENTS

| | | | |
|---|---|---|---|
| 4,273,128 | 6/1981 | Lary | 128/305 |
| 4,411,055 | 10/1983 | Simpson et al. | 29/447 |
| 4,413,989 | 11/1983 | Schjeldahl et al. | 604/96 |
| 4,445,509 | 5/1984 | Auth | 128/305 |
| 4,456,000 | 6/1984 | Schjeldahl et al. | 604/49 X |
| 4,490,421 | 12/1984 | Levy | 128/344 X |
| 4,572,186 | 2/1986 | Gould et al. | 128/341 |
| 4,576,177 | 3/1986 | Webster, Jr. | 128/660 |
| 4,582,181 | 4/1986 | Samson | 128/348.1 |
| 4,587,975 | 3/1987 | Salo et al. | 128/344 |
| 4,589,412 | 5/1986 | Kensey | 128/305 |
| 4,610,662 | 9/1986 | Weikl et al. | 128/348.1 X |
| 4,631,052 | 12/1986 | Kensey | 604/22 |
| 4,636,195 | 1/1987 | Wolinsky | 604/53 |
| 4,641,912 | 2/1987 | Goldenberg | 128/6 X |
| 4,646,742 | 3/1987 | Packard et al. | 128/344 |
| 4,650,466 | 3/1987 | Luther | 604/95 |
| 4,723,549 | 2/1988 | Wholey et al. | 128/344 |

OTHER PUBLICATIONS

Fogarty, et al., Surg., Gynec. & Obstet. 116:241-244 (1963).
Fogarty and Cranley, Annals of Surger 161(3):325-330 (1965).
Hesse and Kletschka, Annals of Surger 155(2):320-322 (1962).

*Primary Examiner*—Michael H. Thaler
*Attorney, Agent, or Firm*—Dorsey & Whitney

[57] ABSTRACT

An angioplasty device is disclosed for treatment of, or for compression and/or removal of an obstruction from, a vessel or vessel-like structure in medical, non-medical and industrial applications. The device incorporates a trap/barrier for trapping and removing particles that break away from the treatment site with traditional angioplasty devices including but not limited to balloons, cutting rotors, fiber meshes, lasers and the like. The device also provides means for removing the trapped particles from the treated vessel. An angioplasty device is also enclosed that incorporates only the trap/barrier and particles removal elements of the previously described device.

A method for treatment of, or for removal or compression of an obstruction in, a vessel or vessel-like structure is disclosed that utilizes an angioplasty device of the instant invention. A method employing an angioplasty device of the instant invention is also disclosed for preventing particles from escaping from a point of manipulation of a vessel or vessel-like structure.

28 Claims, 8 Drawing Sheets

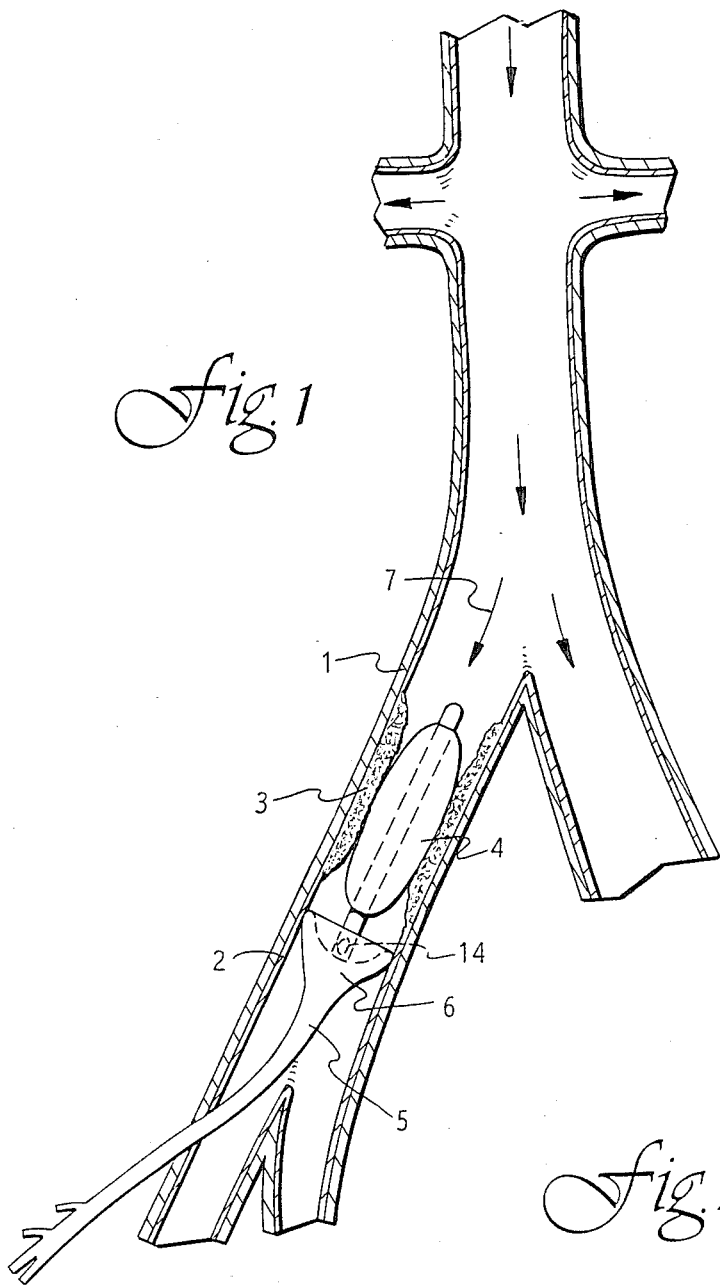
fig.1
fig.2
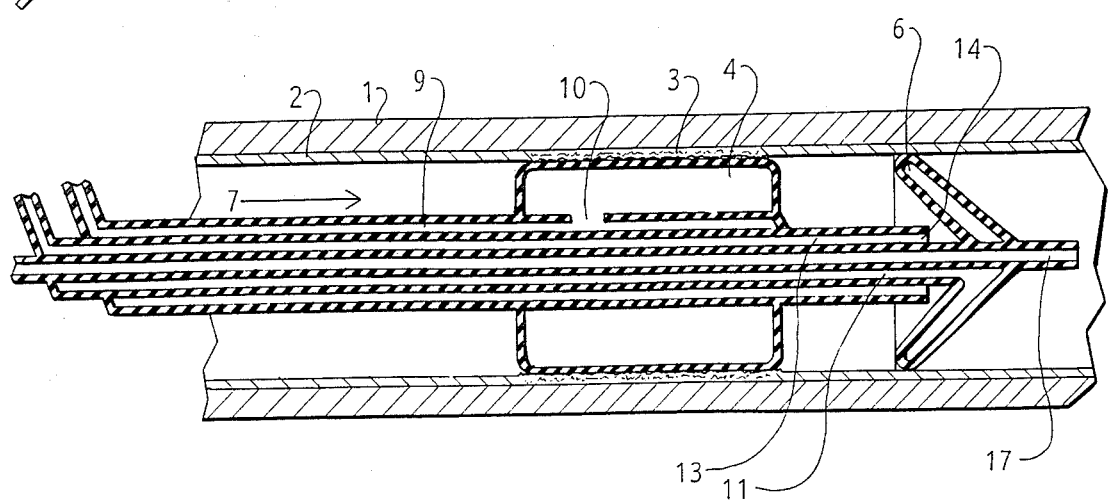

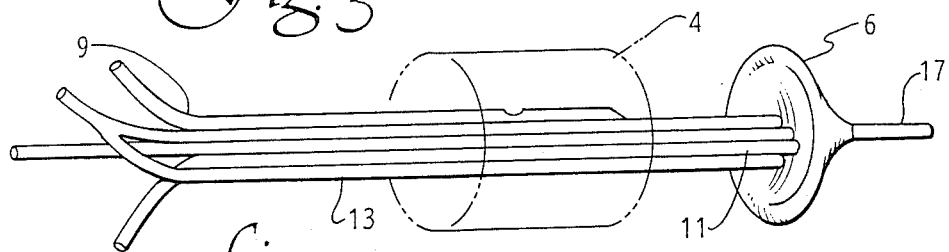
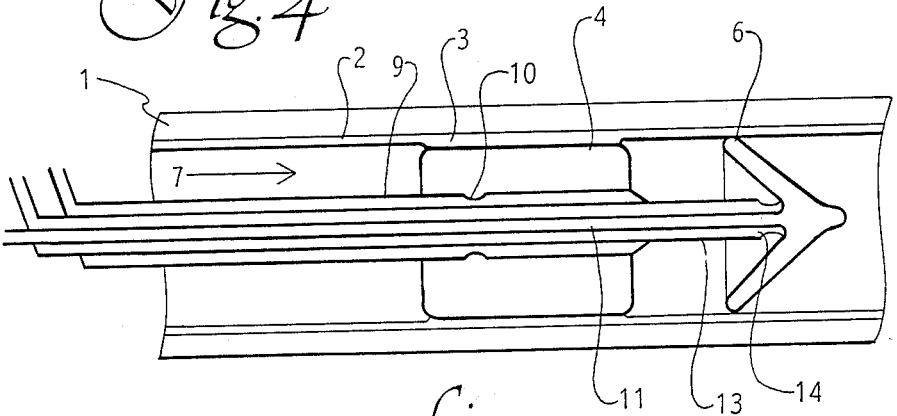
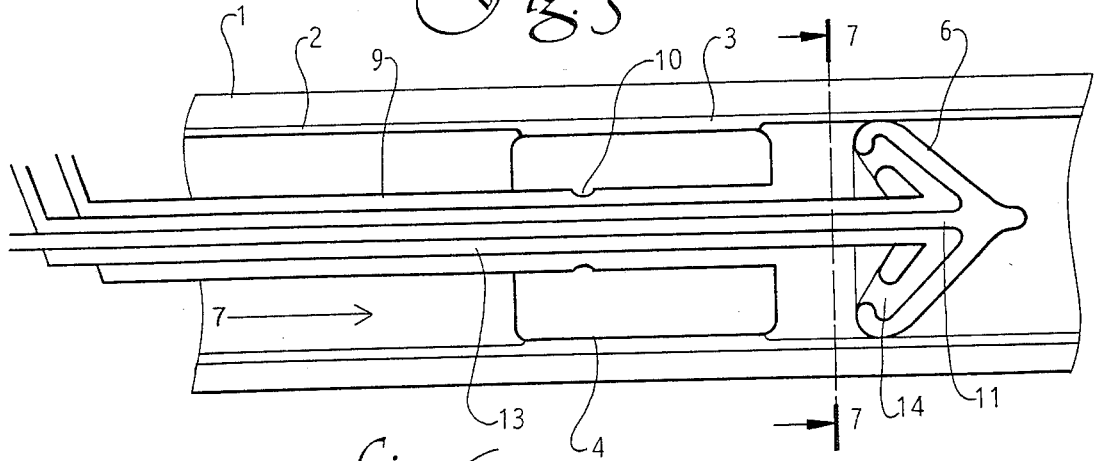
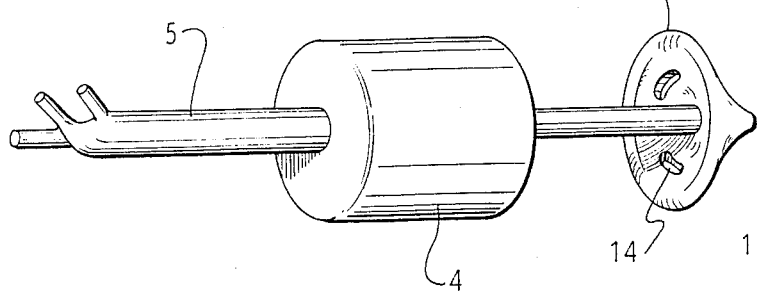
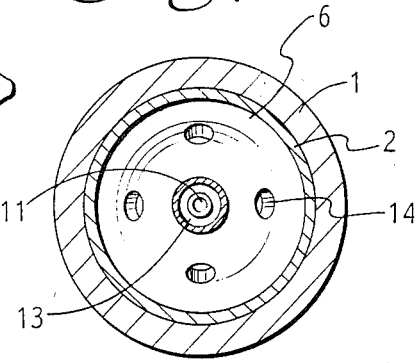

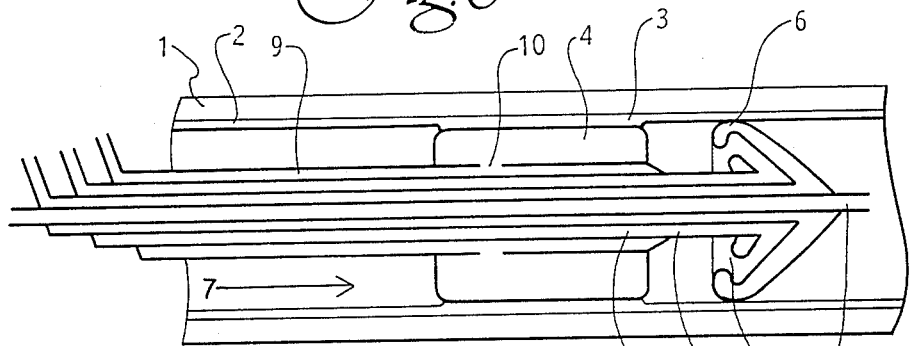
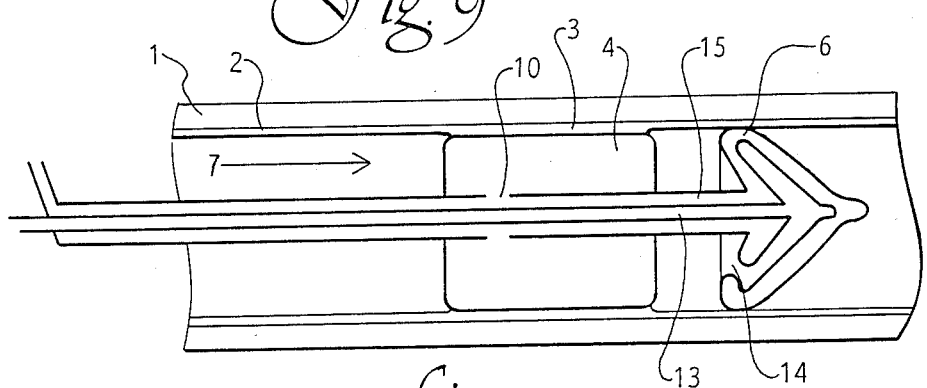
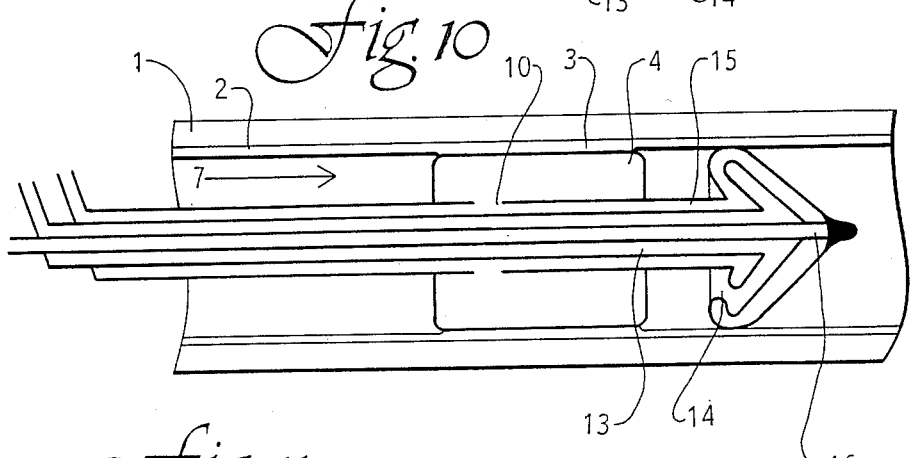
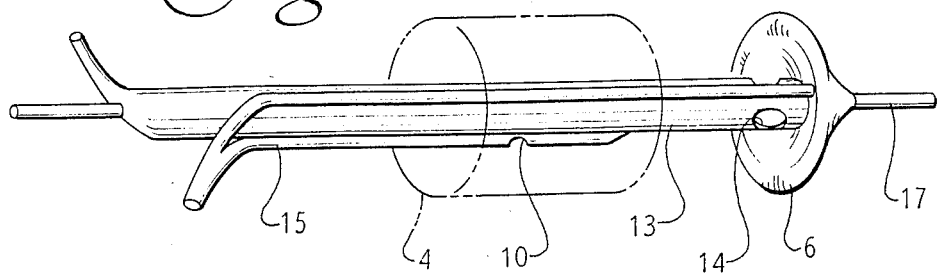

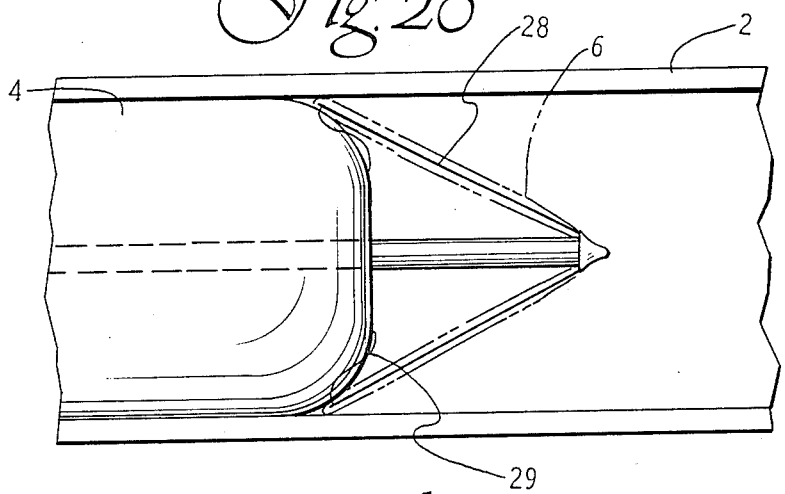
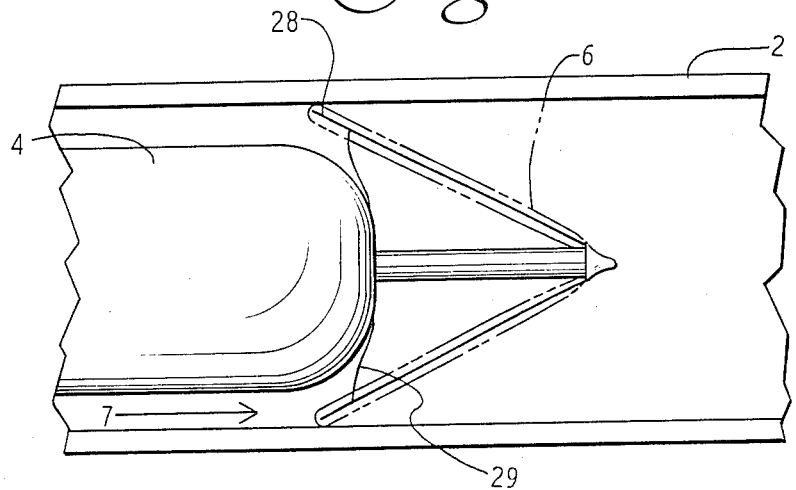
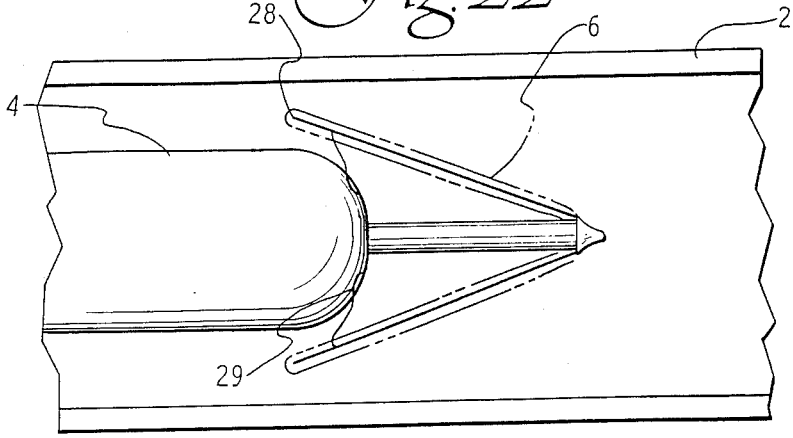

ANGIOPLASTY DEVICE AND METHOD OF USING THE SAME

BACKGROUND OF THE INVENTION

This invention relates to a new and improved angioplasty device for compressing and/or removing atherosclerotic plaques, thromboses, stenoses, occlusions, clots, potential embolic material and so forth (hereinafter "obstructions") from veins, arteries, vessels, ducts and the like (hereinafter "vessels"). The device also has potential for treatment of the following conditions or performance of the following procedures, among others: congenital or acquired stenoses or obstructions; percutaneous aspiration thromboembolectomy; cerebral embolization; congenital or acquired obstruction or stenosis of the aorta, renal, coronary, pulmonary, iliac, femoral, popliteal, peroneal, dorsalis pedis, subclavian, axillary, brachial, radial, ulnar, vertebral, cerebral and-/or cerebellar artery or any other accessible artery or their ramifications; congenital or acquired obstruction or stenosis of the superior vena cava, inferior vena cava, common iliac, internal iliac, external iliac, femoral, greater saphenous, lesser saphenous, posterior tibial, peroneal, popliteal, pulmonary, coronary, coronary sinus, innominate, brachial, cephalic, basilic, internal jugular, external jugular, cerebral, cerebellar, sinuses of the dura mater and/or vertebral vein or any other accessible vein or their ramifications; atheromatous lesions of any graft or its ramifications; obstructions or stenoses of connections between and among grafts, vains, arteries, organs and ducts; vena caval bleeding; congenital or acquired intracardiac obstructions, stenoses, shunts and/or aberrant communications; congenital or acquired cardiovascular obstructions, stenoses and-/or diseases; infusion of thrombolytic agents; thromboembolic phenomena; diagnostic catheterization; removal of clots; intrahepatic and/or extrahepatic biliary ductal obstructions (e.g., stones, sediment or strictures); intravascular, intracardiac and/or intraductal foreign bodies; renal dialysis; congenital and acquired esophageal and/or gastrointestinal obstructions and/or stenoses; non-organized atheromata; dialysis fistula stenosis; ruptured cerebral aneurysm; arterio-arterial, arteriovenous and/or veno-venous fistulae; ureteral obstructions obstructions (e.g., stones, sediment or strictures); fibromuscular dysplasia of the renal artery, carotid artery and/or other blood vessels; and/or atherosclerosis of any accessible artery, vein or their ramifications. Such procedures may be performed in both humans and other applications.

As used throughout this specification and the claims "angioplasty" shall not be restrictive and shall refer to (1) any of the medical and/or veterinary procedures and treatments described in the preceding paragraph, (2) procedures and treatments similar to those described in the preceding paragraph, and (3) any other treatment or procedure involving the removal of an obstruction from vessels or vessel-like structures, regardless of whether such structures are part of or associated with a living organism. It may be obvious to those skilled in fields of art apart from the art of angioplasty devices and procedures that the instant invention could be applied to remove obstructions from "non-living" tubes, tubules, conduits, fibers or other structures (also hereinafter "vessels") in non-medical or industrial applications. For example, a device of the invention could be used to remove an obstruction from a fluid delivery tube within a machine under conditions where it would be undesirable for particles of the obstruction to break free and continue down the tube, e.g., if the machine were still running and particles would jeopardize continued operation. The term "angioplasty" as used throughout this specification and the appended claims is intended to encompass any such applications.

Prior art devices, representing the traditional angioplasty device, are basically a catheter containing a balloon-like member which is inserted into the occluded vessel. Expansion of the balloon at the obstruction site crushes the obstruction against the interior lining of the vessel. When the balloon is retracted, the obstruction remains pressed against the vessel wall and the effective diameter of the vessel through which fluid may flow is increased at the site of the obstruction. The traditional angioplasty device incorporating a balloon is represented by U.S. Pat. Nos. 4,646,742, 4,636,195, 4,587,975 and 4,273,128.

Angioplasty devices have also been developed incorporating expandable meshes or braids, U.S. Pat. Nos. 4,650,466 and 4,572,186, drilling or cutting members, U.S. Pat. Nos. 4,631,052, 4,589,412 and 4,445,509, and lasers, U.S. Pat. Nos. 4,641,912 and 4,576,177, as the means for crushing or removing an obstruction.

Many problems have been associated with all types of angioplasty devices. Perhaps the most significant problem is the creation of particulate matter during the obstruction removal procedure. These particles are released into the fluid flowing through the vessel and can lead to emboli, clots, stroke, kidney failure, heart failure, gangrene, tissue injury, tissue death, emergency bypass surgery, death and other undesirable side effects and complications.

It would be desirable to provide an angioplasty device that prevents substantially all physiologically significant particles from escaping from the obstruction site, thus preventing the occurrence of unfavorable side effects from angioplasty treatment and procedures.

SUMMARY OF THE INVENTION

In accordance with the instant invention, an angioplasty device is disclosed for use in an angioplasty procedure or other medical, veterinary, non-medical or industrial applications where removal of an obstruction from a vessel or vessel-like structure could produce particles which, if allowed to remain in said vessel, could cause undesirable complications and results.

The angioplasty device incorporates an operative member, means for controlling the operative member, a trap/barrier, means for expanding the trap/barrier, means for removing particles, and a catheter bundle. The operative member can be one of many known methods or devices for removing and/or crushing an obstruction in a vessel, including but not limited to balloons, cutting rotors, fiber meshes and lasers. A given operative member is controlled in a device of the instant invention by the same control means previously known for such device or mechanism. In the case of a balloon, at least one canal through which an expansion medium could be injected would be one appropriate control means. For a laser, the appropriate control means would be a switch that turns the laser on.

The trap/barrier serves as (1) a barrier preventing physiologically significant particles breaking away from the obstruction site during an angioplasty procedure or other application of a device of the instant invention from progressing away from the obstruction site and creating complications, and (2) a trap that collects particles so that they can be removed from the treatment site. The trap/barrier can be impervious to fluid flow within the vessel or can be a membrane or similar structure having pores through which the vessel fluid can pass. The trap/barrier is expanded into the proper functional position by an expansion means which can be adapted to suit the nature of the trap/barrier. When the trap/barrier is inflatable, the expansion means is at least one canal through which an expansion medium can be injected. Alternatively, the expansion means can be at least one expansion spring, expansion stent or expansion leaf on or within the trap/barrier. The trap/barrier is expanded as the springs, stents or leaves are pushed outward by the operation of the operative member, fibers, shafts, pods or other means.

In some applications, the control means for a balloon operative member and the expansion means of an inflatable member can both be provided by a bi-functional canal through which an expansion medium can be injected.

Particles are removed from the vessel by at least one particle removal aperture and at least one particle removal canal. A pressure differential is provided between the particle removal canal and the vessel such that particles are pushed or drawn through the particle removal aperture. Alternatively, particles may be collected by the trap/barrier and trapped within it when the trap/barrier is retracted and then removed with the device.

The catheter bundle is a collection of the various canals associated with the various aspects of the device.

Another angioplasty device is also disclosed that incorporates only the trap/barrier, expansion means, particles removal means and catheter bundle.

The instant invention also involves a method for (1) treatment of, or (2) removal or compression of an obstruction in, a vessel or vessel-like structure using an angioplasty device of the instant invention. The angioplasty device is inserted into the vessel and aligned with the treatment or obstruction site. The device is manipulated such that the desired treatment, removal or compression is achieved and particles are collected within or removed into the device. The device is then retracted and removed from the vessel.

The instant invention also provides a method for preventing particles from escaping from a point of manipulation of a vessel or vessel-like structure. A device of the instant invention is inserted into the vessel and expanded at an appropriate point "downstream" or "upstream" from the manipulation site. After the manipulation is completed, the particles are collected and removed into the device. The device is then retracted and removed from the vessel.

BRIEF DESCRIPTION OF THE FIGURES

FIG. 1 shows a cross-sectional fragmentary diagram of the use of a preferred embodiment of the invention.

FIG. 2 is a cross-sectional diagram of a preferred embodiment of the invention.

FIG. 3 is a pictorial view of the preferred embodiment of the invention.

FIG. 4 and FIG. 5 are simplified cross-sectional diagrams of alternative forms of the invention.

FIG. 6 is a pictorial view of an alternative form of the invention.

FIG. 7 is a section taken along line 7—7 of FIG. 5.

FIGS. 8 thru 10 are simplified cross-sectional diagrams of other alternative forms of the invention.

FIG. 11 is a pictorial view of another alternative form of the invention.

FIG. 13b is a cross-sectional diagram of the device of FIG. 13a.

FIGS. 19 through 22 are pictorial views of an alternative mechanism for expanding the trap/barrier of the instant invention.

DETAILED DESCRIPTION OF THE INVENTION

Figure 12:
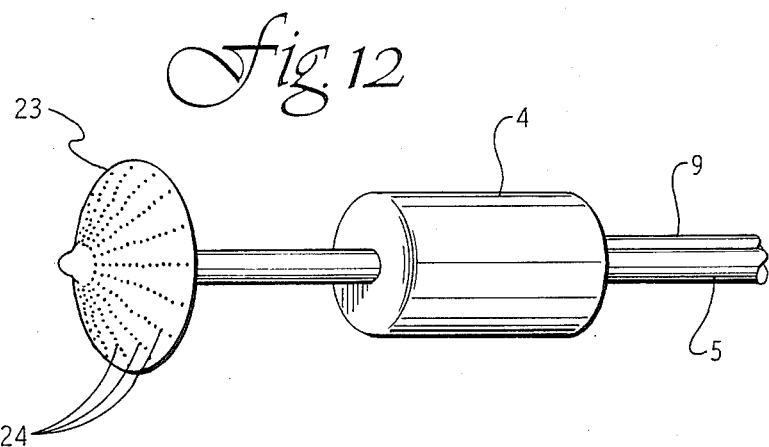
FIG. 12 is a pictorial view of an alternative trap/barrier.

The angioplasty device of the present invention can take many forms, each of which includes a structure that serves as (1) a barrier preventing physiologically significant particles breaking away from the obstruction site during an angioplasty procedure or other application of a device of the instant invention from progressing away from the obstruction site and creating complications, and (2) a trap that collects physiologically significant particles so that they can be removed from the treatment site. A particle is "physiologically significant" if it could potentially cause damage or other unwanted complication if it were to migrate from the obstruction site. Particles produced from an obstruction or any other particles breaking away from the interior of a vessel in which a device of the instant invention is used are hereinafter generically referred to as "particles".

FIG. 1 shows an example of the use of a preferred embodiment of the instant invention. The device is inserted into a vessel 1 according to methods well known to those skilled in the art. The device may be inserted at any point in relation to the obstruction site 3 that is consistent with the desired treatment protocol. The balloon 4 is aligned with the site of the obstruction 3 using methods well known in the art. The device is then oriented such that the trap/barrier 6, which serves the trap/barrier functions, is situated in a retrograde direction, "downstream" in relation to the direction of fluid flow 7, from the obstruction site 3. The embodiment of FIG. 1 allows insertion of the balloon 4 before the trap/barrier 6 from a point "downstream" from the obstruction site 3.

Fluid, air or other expansion medium is injected into the device through canals in the catheter bundle 5 such that the trap/barrier 6 is expanded first, so that it forms a seal against the vessel inner lining 2, followed by the balloon 4. Alternatively, both the trap/barrier 6 and the balloon 4 could be expanded simultaneously or the balloon 4 could be expanded before the trap/barrier 6. If, however, substantially all of the physiologically significant particles breaking away from the obstruction site 3 are to be trapped by the trap/barrier 6, as is the preferred operation of devices of the invention, the trap/barrier 6 should be fully expanded before the balloon 4 is fully expanded.

As the balloon 4 is expanded the obstruction 3 is crushed against the vessel inner lining 2 such that the effective inner diameter of the vessel 1 through which fluid can flow is increased. Crushing of the obstruction 3 creates particles which may break free on either side of the balloon 4.

The balloon 4 is then partially retracted. The particles of the obstruction are then, according to the preferred embodiment, pushed toward the trap/barrier 6 by the fluid pressure in the vessel 1, or, according to an alternative embodiment, drawn toward the trap/barrier 6 by providing a pressure differential between the vessel and canals within the catheter bundle 5. The particles are either pushed or drawn into the catheter bundle 5 through a particle removal aperture 14 from which they may be disposed of, or lodged in the trap/barrier 6 such that, when it is retracted, the particles are trapped inside and removed with the trap/barrier 6.

The balloon in a device of the instant invention serves as an operative member which may be replaced by any means known in the art, or later developed in the art, for removing or compressing an obstruction. As used throughout this specification and the claims, the term "operative member" shall encompass any means for removing or compressing an obstruction, including but not limited to the means represented by U.S. Pat. Nos. 4,646,742, 4,636,195, 4,587,975, 4,273,128, 4,650,466, 4,572,186, 4,631,052, 4,589,412, 4,445,509, 4,641,912 and 4,576,177, the disclosures of which are incorporated herein by reference, which include balloons, meshes, cutting rotors and lasers. Each type of operative member will have its unique control mechanism that, in the case of a balloon, fills it or, in the case of a laser or cutting rotor, turns it on. These various mechanisms are referred to herein collectively as "control means." Although the balloon and its associated filling or expansion system will be used throughout the specification as an example of an operative member and its associated control means, it is to be understood that any available operative member and its control means could be substituted in many of the embodiments discussed herein. References to "expansion" and "retraction" of the balloon should be understood to, by inference, refer to activating and deactivating whatever operative member is incorporated into a given device.

Although the figures depict the trap/barrier 6 as having a generally conical shape, the trap/barrier 6 can be any shape as long as a seal is achieved with the inner lining of the vessel 2 to be treated and the shape facilitates entrapment of the particles. Further, although the figures depict the trap/barrier 6 and operative means, in most cases a ballon 4, as being spatially remote from each other, the trap/barrier 6 and operative means may be situated with respect to each other in any configuration that allows the trap/barrier 6 to achieve a seal with the inner vessel lining 2 and to trap particles when expanded.

FIGS. 2 and 3 depict another preferred embodiment of the invention, including detail within the catheter bundle 5. In contrast with the preferred embodiment depicted in FIG. 1, the preferred embodiment depicted in FIGS. 2 and 3 allows insertion of the trap/barrier 6 before the balloon 4 from a point "upstream" from the obstruction site 3. By changing the relative location of the trap/barrier and the operative member in a given device, an obstruction can be treated by approaching from the most advantageous direction in the vessel. The trap/barrier 6 is expanded by introduction of an expansion medium into the trap/barrier expansion canal 11 which fills the trap/barrier 6. The balloon 4 is expanded by introduction of an expansion medium into the balloon expansion canal 9 which fills the balloon 4 through the balloon expansion aperture 10, thus crushing the obstruction 3 against the vessel inner lining 2. When the vessel is living tissue, e.g., a human or animal vein, artery or duct, the balloon 4 is inflated to a pressure ranging preferably from approximately 3 to 15 atmospheres, or more depending on the application. The proper pressure will be dependant on the treatment protocol, the type of organism being treated, the type of vessel being treated and the material from which the balloon is constructed. Appropriate expansion pressures for a given situation will be obvious to those skilled in the art.

After the balloon 4 is partially retracted, any particles are pushed toward the trap/barrier 6 by the fluid flow 7 in the vessel. The particle removal aperture 14 and particle removal canal 13 are open and, since the trap/barrier 6 is blocking the normal fluid flow 7, the particles and some fluid are pushed through the particle removal aperture 14 and out the particle removal canal 13 for disposal. Those particles not pushed through the particle removal aperture 14 are pushed into the apex of the trap/barrier 6 where they can be trapped after the trap/barrier 6 is retracted. As an alternative, the particle removal canal 13 can be attached to means for providing a pressure differential between the vessel pressure and the particle removal canal 13 that will actively draw the particles and some fluid from the vessel for disposal. As another alternative, the device can include as many particle removal apertures and canals as can be incorporated into the device.

The preferred embodiment also incorporates a flow-through canal 17 which can be used for introduction of medicinal agents, taking samples of fluid, introducing a guide wire to assist insertion of the angioplasty device, or for any other desirable purpose.

FIG. 4 depicts an alternative embodiment of the invention in which the flow-through canal 17 has been eliminated. FIG. 4 and the remaining cross sectional figures have been simplified in comparison with FIG. 2 by omission of any indication of the thickness of the walls forming the various canals, chambers and members incorporated into the depicted devices.

FIGS. 5 and 6 show an embodiment of the invention wherein the particle removal apertures 14 have been incorporated into the trap/barrier 6. The particle removal apertures 14 can be of any shape and arranged in any formation within the trap/barrier 6 that allows the fluid flow in the vessel or a provided pressure differential to draw particles into the apertures. As many apertures may be used as may be incorporated into the device while still maintaining functionality. A conical shape of the trap/barrier 6 facilitates introduction of the particles into the particle removal apertures 14, but is not essential.

FIG. 7 shows an example of one possible orientation of the particle removal apertures 14 within the trap/barrier 6.

FIG. 8 depicts an embodiment of the invention with a flow-through canal 17 and having the particle removal apertures 14 situated in the trap/barrier 6.

FIG. 9 depicts an embodiment of the invention wherein both the balloon 4 and the trap/barrier 6 are expanded by infusion of an expansion medium through a bi-functional expansion canal 15. The balloon 4, trap/barrier 6 and bi-functional expansion canal 15 should be of proper size, configuration and design so as to expand the balloon 4 and trap/barrier 6 in the desired order, and such that the balloon 4 can be partially retracted while leaving the trap/barrier 6 fully expanded so as to allow collection of particles.

FIG. 10 depicts an embodiment of the invention as shown in FIG. 9 with the addition of a guide wire canal 16 into which a guide wire can be inserted to facilitate insertion and positioning of the device.

FIG. 11 depicts an embodiment of the invention with a bifunctional expansion canal 15 for the balloon 4 and the trap/barrier 6. The bi-functional expansion canal 15 has been bifurcated. The embodiment of FIG. 11 also has a different type of particle removal aperture 14 which is not situated in the trap/barrier 6. Finally, the depicted embodiment incorporates a flow-through canal 17.

FIG. 12 depicts another embodiment of the invention wherein the trap/barrier is a trap/barrier membrane 23. The configuration of particle removal apertures and canals normally associated with the trap/barrier is not included. The trap/barrier membrane 23 has one or more pores 24 through which fluid, substances in the fluid and physiologically insignificant particles can pass. When the balloon 4 is partially retracted, fluid flow 7 and its associated pressure will resume and the trap/barrier membrane 23 will act as a sieve, collecting all physiologically significant particles that were released. When the trap/barrier membrane 23 is retracted, the trapped particles are held and can be removed with the angioplasty device.

The size of the pores 24 can be varied depending upon the use of the device. The pores 24 should be small enough to trap all physiologically significant particles. The location of the obstruction site relative to areas where renegade particles could cause undesirable complications will determine what size particle is physiologically significant. In a traditional angioplasty procedure, the pore size could be approximately $2\mu$ in diameter. A $2\mu$ pore would trap any particle large enough to block capillaries (diameter approximately $3-4\mu$). Larger pore sizes may be appropriate in other medical or non-medical applications of the device of the invention. The appropriate pore size for a given application should be obvious to those skilled in various fields of art to which the invention could be applied.

A trap/barrier could also be substituted for the trap/barrier membrane 23 in an embodiment like that of FIG. 12. The device would not include any particle removal apertures or canals. Particles would be pushed into the trap/barrier where they could be trapped when the device is retracted and removed. In such an embodiment the conical shape of the trap/barrier would be very important. Blind pockets or sinuses could also be incorporated into the trap/barrier or the side of the catheter bundle to facilitate the lodgement of the debris in a favorable position to be sequestered from being swept away as the trap/barrier is retracted and removed. As the trap/barrier is retracted, it would cover over the particles, enclosing them. Similar features could also be incorporated with a trap/barrier membrane.

Figure 13A:
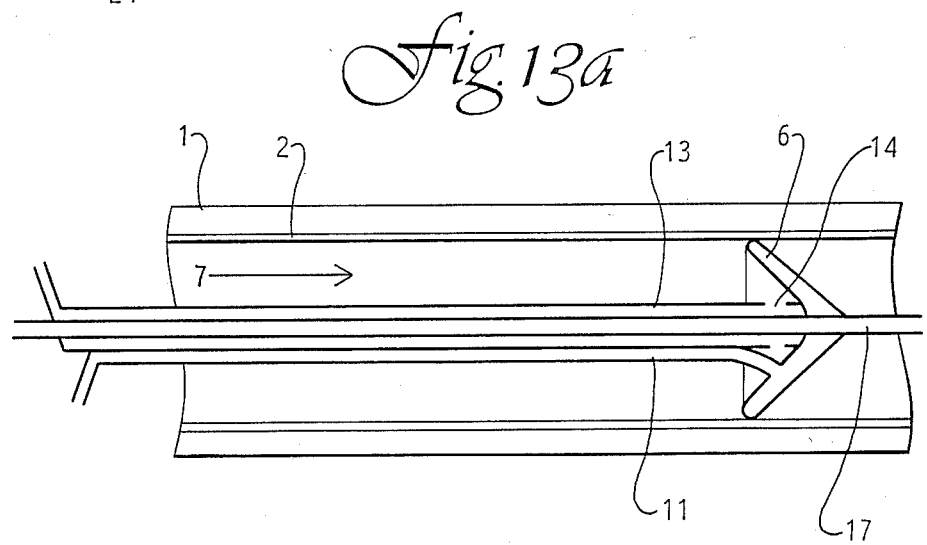
FIG. 13a is a pictorial view of another alternative form of the invention.
Figure 13B:
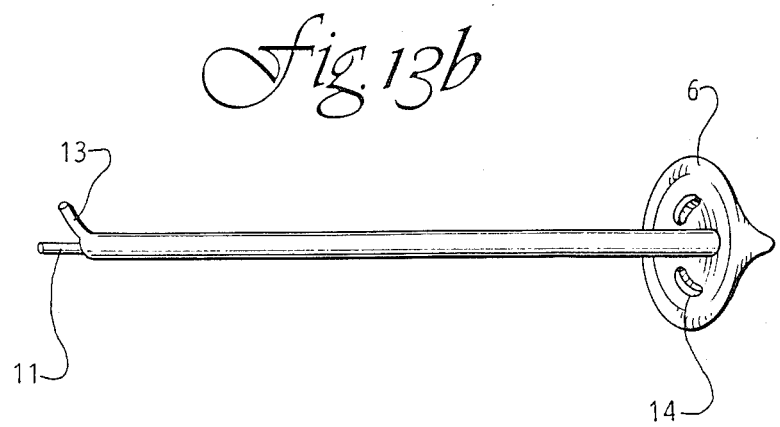

FIG. 13 depicts an embodiment of the invention incorporating only the trap/barrier 6, catheter bundle 5, trap/barrier expansion canal 11, trap/barrier interior chamber 12, particle removal apertures 14 and particle removal canal 13. This embodiment could be used with many angioplasty devices currently in use, which would provide the means for compressing or removing an obstruction. The trap/barrier device of this embodiment could be inserted through a central canal in a traditional angioplasty device such that it can be expanded "downstream" from the obstruction site. Obviously, the trap/barrier membrane 23 could be substituted for the trap/barrier 6 in this embodiment.

The embodiment depicted in FIG. 13 and similar embodiments could be used as a trap and trap/barrier in any situation where it is possible to create particles, not necessarily from an obstruction, which could cause undesirable complications if not removed. For example, in any procedure that involves clamping of a blood vessel, particles can break free from materials that have accumulated within but do not appreciably obstruct the vessel. Those particles could cause the same complications associated with renegade particles breaking away from an obstruction during a traditional angioplasty procedure. A device like that in FIG. 13 could be inserted "downstream" or "upstream" from the clamp site to trap and remove any particles that break free. Although this type of application involves no operative means as herein defined, such an application and similar applications, including medical, veterinary, non-medical and industrial applications, are intended to be encompassed by the term "angioplasty" as used throughout this specification and the appended claims. Moreover, many of the characteristics and features described throughout the specification could also be incorporated into a device for such applications.

It is important to note that, in any embodiment of the invention, the various canals contained within the catheter bundle 5 can either be arranged (1) concentrically, such that they all share the same central axis, (2) separately, such that each canal is independent of all the others, or (3) some combination of concentric and separate canal structures. The collection of canals, whether arranged concentrically, separately or both, is referred to throughout this specification and the appended claims as the catheter bundle 5.

The trap/barrier 6 or trap/barrier membrane 23 in any embodiment of the invention may be designed or expanded in any manner that will achieve a shape that forms a seal with with the interior lining of the vessel 2 to be treated. By using methods known to those skilled in the art of manufacturing similar devices and components, the manner in which the trap/barrier 6 or trap/barrier membrane 23 is manufactured can cause the trap/barrier 6 or trap/barrier membrane 23 to expand so as to achieve the desired shape and seal without any underlying supporting expansion mechanism.

Figure 14:
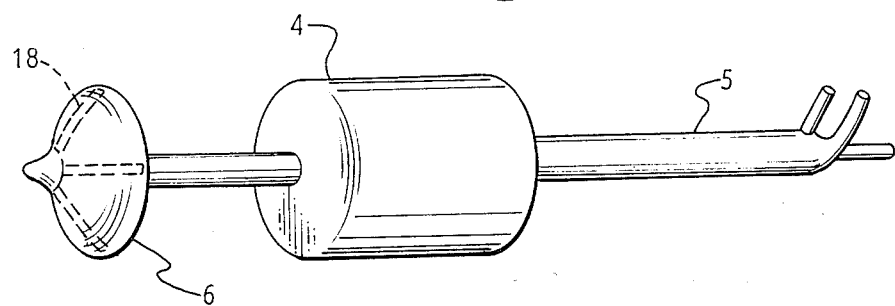
FIG. 14 is a fragmentary pictorial view of an alternative form of the invention.

Alternatively, the trap/barrier 6 or trap/barrier membrane 23 can be expanded with a supporting expansion mechanism. FIGS. 14 through 18 depict some possible supporting expansion mechanisms. FIG. 14 depicts a plurality of expansion springs 18 that expand the trap/barrier 6. The expansion springs 18 could be manufactured from plastic, metal or any other material that could be manufactured to hold the desired shape of the trap/barrier 6. The expanded position would be the "natural" position of the expansion springs 18. The device would also incorporate means for pulling the springs into a retracted position for insertion and removal of the device from the vessel. The retraction means could be fibers that extend back from the expansion springs 18, a sheath that covers the springs and holds them down until expansion, or other means which will be obvious to those skilled in the art.

Figure 15:
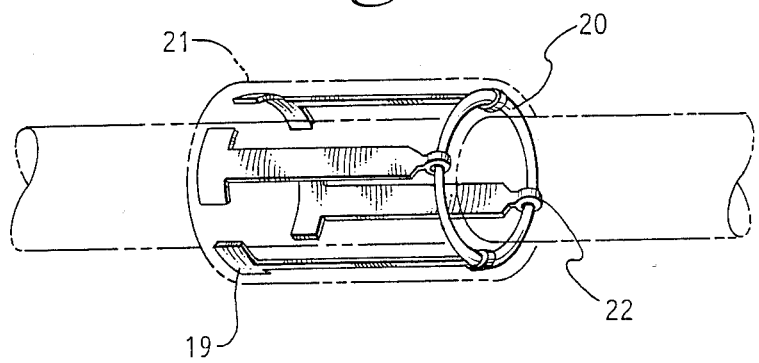
FIG. 15 is a pictorial view of a mechanism for expanding the trap/barrier of a device of the instant invention.
Figure 16:
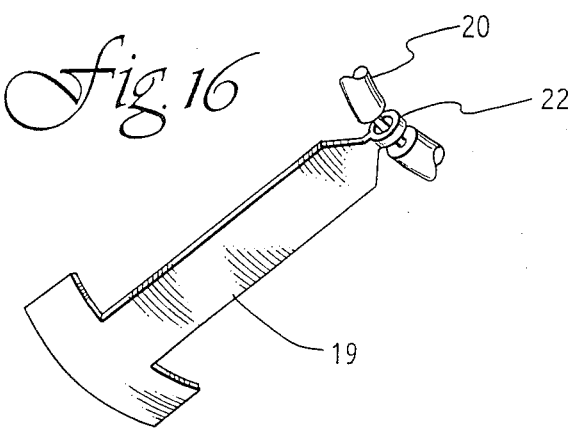
FIG. 16 is a perspective view of a component of the mechanism depicted in FIG. 15.
Figure 17:
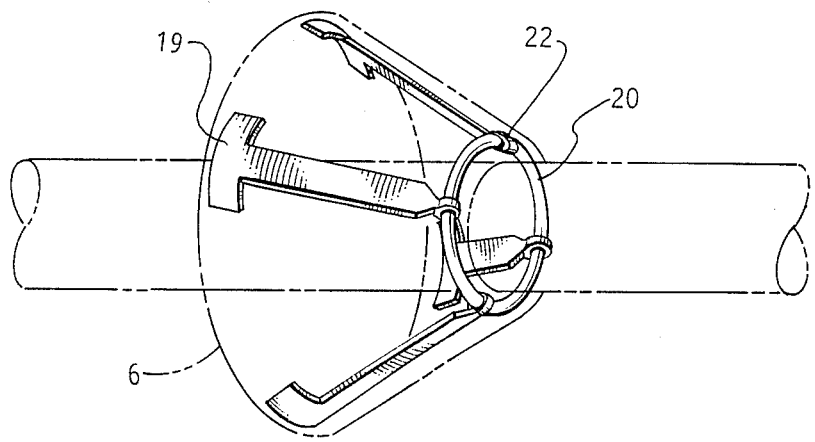
FIG. 17 is a pictorial view of the expanded mechanism of FIG. 15.

FIGS. 15 through 17 depict an assembly comprising a plurality of expansion stents 19 and a stent ring 20 situated inside the retracted trap/barrier 6. The stents can again be made of plastic, metal or any other material of suitable character to give the trap/barrier 6 the desired shape. Each expansion stent 19 is attached to the stent ring 20 by a stent hinge 22 which allows movement of the expansion stent 19 to the expanded position without moving circumferentially around the stent ring 20. FIG. 17 depicts the expanded position of the stent assembly.

Figure 18:
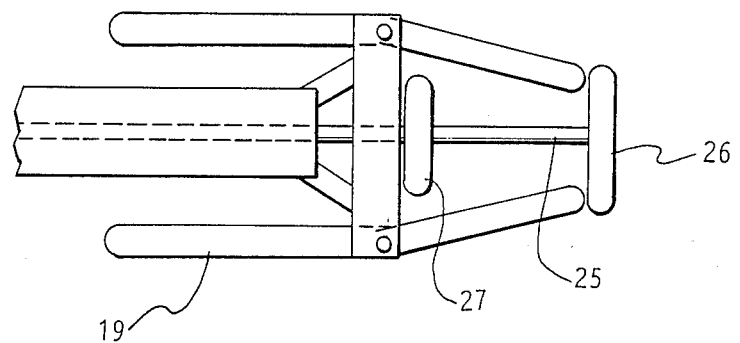
FIG. 18 is a pictorial view of an alternative mechanism for expanding the trap/barrier of the instant invention.
Figure 19:
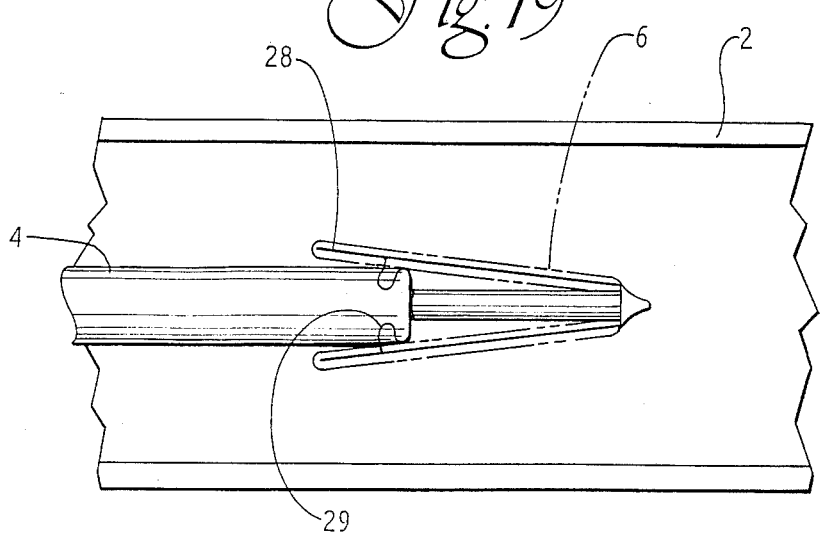

FIG. 18 depicts another supporting expansion mechanism. The assembly contains a plurality of expansion stents 19 which are attached to a stent ring 20. Centered within the stent ring 20 is an expansion shaft 25 having an expansion node 26 and a retraction node 27. The expansion shaft 25 extends back through the catheter bundle 5 such that it may be manipulated. When the expansion shaft 25 is pulled away from the trap/barrier 6, the expansion node 26 engages the expansion stents 19 and pushes them outward, thus expanding the trap/barrier 6. When the expansion shaft 25 is pushed toward the trap/barrier 6, the retraction node 27 engages the expansion stents 19 and pushes them inward, thus retracting the trap/barrier 6. A canal could be included through the expansion shaft 25 for insertion of a guide wire.

If properly situated with respect to the balloon 4, the trap/barrier 6 could also be expanded and retracted by the action of the balloon 4 as the balloon 4 is expanded and retracted. FIGS. 19 through 22 depict an expansion means comprised of a plurality of expansion leaves 28 and shroud lines 29. The expansion leaves 28 should be made from a formable material that will give support to the trap/barrier 6, yet assume any position or shape into which it is formed. In FIGS. 19 through 22, the expansion leaves 28 are attached at one end to the tip of the trap/barrier 6. The other end rests on or near the retracted balloon 4. As the balloon 4 is expanded, it pushes the expansion leaves 28 into a position where they bring the trap/barrier 6 into contact with the inner vessel lining 2 as shown in FIG. 20. The shroud lines 29 are slack. After the obstruction is crushed, as shown in FIG. 21, the balloon 4 is partially retracted such that fluid flow 7 and its associated pressure is partially restored and pushes the particles toward the trap/barrier 6 for removal as previously discussed. Since the expansion leaves 28 are made of a formable material, they maintain the shape into which they were pushed by the balloon 4 and maintain the seal with the inner vessel lining 2. The shroud lines 29 remain slack. When the particles have been collected and/or removed as previously discussed, the balloon 4 is retracted further such that the shroud lines 29 become taut and retract the expansion leaves 28 as shown in FIG. 22. Features from other expansion means could also be combined with an expansion leaf/shroud line configuration to provide the appropriate degree of control over expansion and retraction of the trap/barrier. The degree to which the balloon 4 should be expanded or retracted to cause the expansion means to properly function will be dependant upon the specific design of the device and should be obvious to those skilled in the art once a device design has been chosen and developed.

Figure 23:
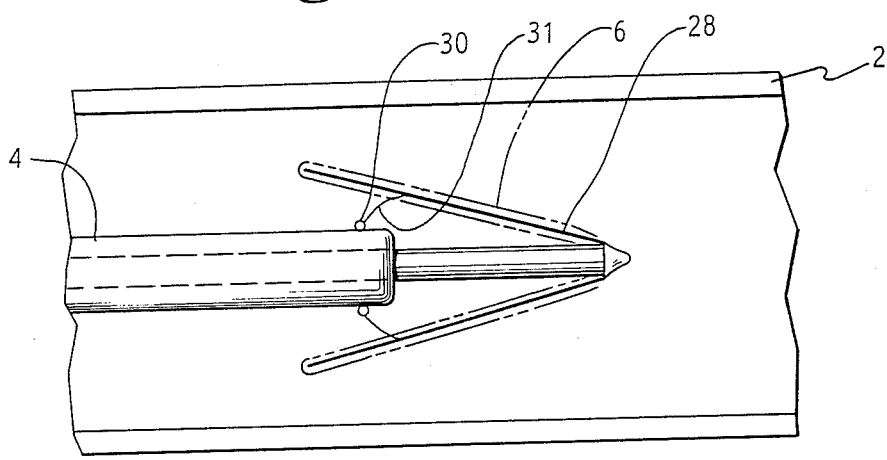
FIG. 23 through 25 are pictorial views of an alternative mechanism for expanding the trap/barrier of the instant invention.
Figure 24:
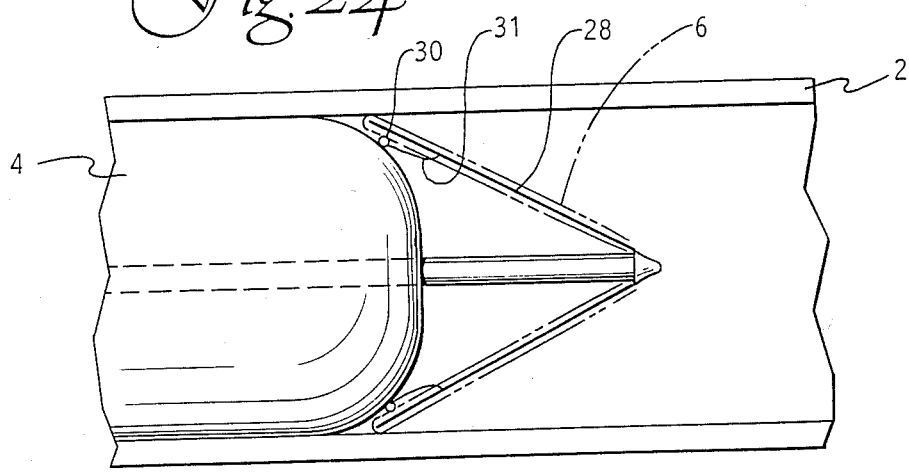
Figure 25:
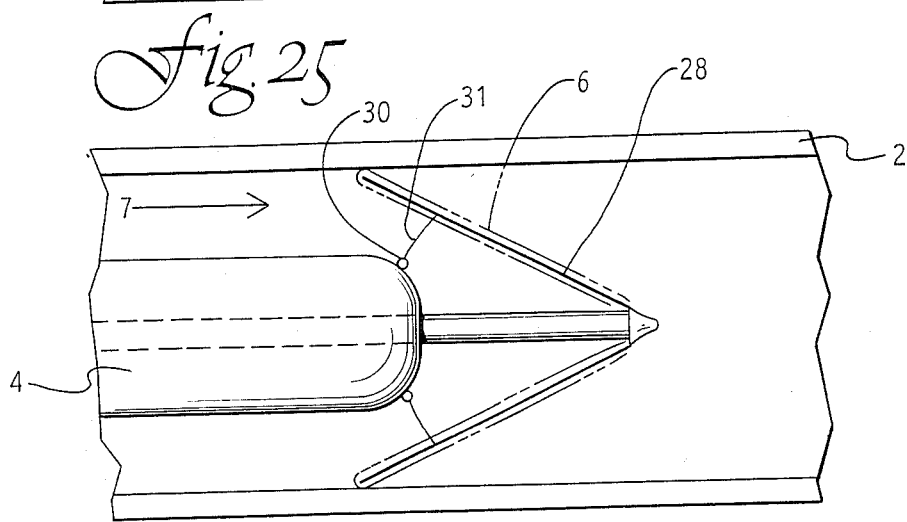

Alternatively, the expansion leaves 28 could be constructed from a material that is rigid and not significantly formable similar to materials that could be used to make the expansion springs 18 of FIG. 14. The expansion leaves 28 are, however, manufactured such that their natural shape would retain the trap/barrier 6 in its retracted position. The expansion leaves 28 do not directly make contact with the balloon 4. Each expansion leaf 28 is fitted with a pod 30 that rests on the surface of the balloon 4 as shown in FIG. 23. Alternatively, the pod could fit into a recess in the side of the catheter such that the expansion leaf lies flush against the catheter when in the retracted state, thus allowing smoother insertion of the catheter. The pod 30 is attached to the expansion leaf 28 by a flexible pod arm 31. As the balloon 4 expands, the pod 30 moves along the surface of the balloon 4 and the trap/barrier 6 is pushed into its expanded position as shown in FIG. 24. When the balloon 4 is fully expanded, the pod arm 31 would be bent such that the pod 30 is pressed toward the expansion leaf 28 out of its natural position as shown in FIG. 24. As the balloon 4 is retracted, the pod arm 31 will return toward its natural position while keeping the expansion leaf 28 in contact with the inner vessel lining 2 as shown in FIG. 25. Fluid flow 7 and its associated pressure will be partially restored and particles can be trapped and disposed of as previously discussed. When the balloon 4 is retracted further, the pod arm 31 completely returns to its natural position and the expansion leaf 28 will return to its natural position, as shown in FIG. 23, thus retracting the trap/barrier 6. The degree to which the balloon 4 should be expanded or retracted to cause the expansion means to properly function will be dependant upon the specific design of the device and should be obvious to those skilled in the art once a specific device design has been chosen and developed.

Alternatively, the pod arm 31 could be eliminated and the pod 30 could be attached to the balloon 4. As the balloon 4 is expanded, the pod 30 pushes the expansion leaf 28 into an expanded position. The pod 30 should be placed on the balloon surface such that the balloon 4 can be partially retracted without breaking the seal between the trap/barrier 6 and the vessel inner lining 2, thus allowing particles to be collected. Methods for choosing proper placement of the pod 30 on the balloon 4 will be obvious to those skilled in the art when considering the type and form of the balloon used in a given device.

Variations of these examples and other means for using the balloon 4 as the force driving an expansion means for the trap/barrier will be obvious to those skilled in the art and are intended to be included within the bounds of the instant invention as defined by the appended claims. Particularly, the expansion stents, expansion springs and expansion leaves described herein can be made of, for example, (1) a deformable material so that they have no "natural" shape and can be freely pushed into desired shapes, (2) a formed material having a "natural" shape that holds the trap/barrier in an expanded position, or (3) a formed material having a "natural" shape that holds the trap/barrier in a retracted position. These and other types of materials may be appropriate and will be obvious to those skilled in the art.

As the preceding discussion of the preferred and alternative embodiments discloses, there are many different structures, configurations and characteristics of the various embodiments of the instant invention, each of which can be individually combined with any of the others to create a device that has the desired characteristics for the desired application. All of the figures and embodiments particularly described herein are meant to be illustrative of the wide range of separate characteristics which can each be individually incorporated into a device of the instant invention and not to in any way restrict combination of such features in devices not particularly described herein.

From the foregoing, it will be obvious to those skilled in the art that various modifications in the above described methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. An angioplasty device for removing an obstruction from a vessel or vessel-like structure comprising:
   a. a catheter bundle for insertion into said vessel;
   b. an operative member, for removal or compression of said obstruction, connected to said catheter bundle;
   c. control means, connected to said operative member, for manipulating said operative member;
   d. a trap/barrier connected to said catheter bundle;
   e. expansion means, connected to said trap/barrier, for expanding and/or retracting said trap/barrier; and
   f. at least one particle removal aperture situated within said trap/barrier for removal of particles.

2. The angioplasty device of claim 1 wherein said operative member is a balloon.

3. The angioplasty device of claim 2 wherein said control means comprises an expansion canal situated within said catheter bundle and connected to said operative member by an expansion aperture.

4. The angioplasty device of claim 2 wherein said expansion means comprises:
   i. at least one expansion leaf situated on or within said trap/barrier; and
   ii. at least one shroud line connecting said expansion leaf and said balloon,
such that expansion and retraction of said balloon expands and retracts said trap/barrier, respectively, and such that upon partial retraction of said balloon physiologically significant particles are moved toward said trap/barrier by pressure within said vessel.

5. The angioplasty device of claim 2 wherein said expansion means comprises:
   i. at least one expansion leaf situated on or within said trap/barrier;
   ii. at least one pod, said pod being (A) attached to said expansion leaf and in contact with or attached to said balloon, or (B) attached to said balloon and in contact with or attached to said expansion leaf,
such that expansion and retraction of said balloon expands and retracts said trap/barrier, respectively, and such that upon partial retraction of said balloon physiologically significant particles are moved toward said trap/barrier by pressure within said vessel.

6. The angioplasty device of claim 1 wherein said expansion means comprises an expansion canal situated within said catheter bundle and connected to said trap/barrier.

7. The angioplasty device of claim 1 wherein said control means and said expansion means comprise a bi-functional expansion canal connected to both said operative member and said trap/barrier.

8. The angioplasty device of claim 1 wherein said expansion means comprises a supporting expansion mechanism for expansion of said trap/barrier.

9. The angioplasty device of claim 8 wherein said supporting expansion mechanism comprises at least one expansion stent situated within or on said trap/barrier such that, when the trap/barrier is expanded, said trap/barrier establishes a seal against the inner lining of the vessel.

10. The angioplasty device of claim 9 wherein said supporting expansion mechanism additionally comprises an expansion shaft, situated within said catheter bundle, having an expansion node and a retraction node such that, when said shaft is moved, said expansion node and said retraction node expand and retract, respectively, said trap/barrier.

11. The angioplasty device of claim 1 wherein said trap/barrier comprises a membrane with at least one pore through which no physiologically significant particles can pass.

12. The angioplasty device of claim 1 further comprising a particle removal canal contained within said catheter bundle and wherein said at least one particle removal aperture is connected to said particle removal canal.

13. The angioplasty device of claim 12 wherein said particle removal aperture is integrated into said trap/barrier.

14. The angioplasty device of claim 12 or 13 wherein said particle removal aperture is connected to means for providing a pressure differential between the fluid in said vessel and said particle removal aperture such that fluid containing particles moves into said aperture.

15. The angioplasty device of claim 1 additionally comprising at least one additional canal situated within said catheter bundle, said additional canal being selected from the group of guide wire canals and flow-through canals.

16. An angioplasty device for removing an obstruction from a vessel or vessel-like structure comprising:
   a. a catheter bundle for insertion into said vessel;
   b. a trap/barrier connected to said catheter bundle;
   c. expansion means, connected to said trap/barrier, for expanding and/or retracting said trap/barrier; and
   d. at least one particle removal aperture situated within said trap/barrier for removal of particles.

17. The angioplasty device of claim 16 wherein said expansion means comprises an expansion canal situated within said catheter bundle and connected to said trap/barrier.

18. The angioplasty device of claim 16 wherein said expansion means comprises a supporting expansion mechanism for expansion of said trap/barrier.

19. The angioplasty device of claim 18 wherein said supporting expansion means comprises at least one expansion stent situated on or within said trap/barrier such that, when the trap/barrier is expanded, said trap/barrier establishes a seal against the inner lining of the vessel.

20. The angioplasty device of claim 19 wherein said supporting expansion means additionally comprises an expansion shaft, situated within said catheter bundle, having an expansion node and a retraction node such that, when said shaft is moved, said expansion node and said retraction node expand and retract, respectively, said trap/barrier.

21. The angioplasty device of claim 16 wherein said trap/barrier comprises a membrane with at least one pore through which no physiologically significant particles can pass.

22. The angioplasty device of claim 16 further comprising a particle removal canal contained within said catheter bundle and wherein said at least one particle removal aperture is connected to said particle removal canal.

23. The angioplasty device of claim 22 wherein said particle removal aperture is integrated into said trap/barrier.

24. The angioplasty device of claim 22 or 23 wherein said particle removal aperture is connected to means for providing a pressure differential between the fluid in said vessel and said particle removal aperture such that fluid containing particles moves from the vessel into said aperture.

25. The angioplasty device of claim 16 additionally comprising at least one additional canal situated within said catheter bundle, said additional canal being selected from the group of guide wire canals and flow-through canals.

26. A method for treatment of, or for removal or compression of an obstruction in, a vessel or vessel-like structure comprising:
   a. inserting an angioplasty device into said vessel;
   b. aligning said device with the site of treatment or the site of the obstruction;
   c. manipulating said device such that the desired treatment, removal or compression is achieved;
   d. removing any resulting particles through or to within said device;
   e. retracting said device; and
   f. removing said device from said vessel carrying any collected particles therewith,
said device comprising:
   i. a catheter bundle for insertion into said vessel;
   ii. an operative member, for removal or compression of said obstruction, connected to said catheter bundle;
   iii. control means, connected to said operative member, for manipulating said operative member;
   iv. a trap/barrier connected to said catheter bundle;
   v. expansion means, connected to said trap/barrier, for expanding and/or retracting said trap/barrier; and
   vi. at least one particle removal aperture situated within said
   trap/barrier for removal of particles.

27. A method for treatment of, or for removal or compression of an obstruction in, a vessel or vessel-like structure comprising:
   a. inserting an angioplasty device into said vessel;
   b. aligning said device with the site of treatment or the site of the obstruction;
   c. expanding said device such that the desired treatment, removal or compression is achieved;
   d. removing any resulting particles through or to within said device;
   e. retracting said device; and
   f. removing said device from said vessel,
said device comprising:
   i. a catheter bundle for insertion into said vessel;
   ii. a trap/barrier connected to said catheter bundle;
   iii. expansion means, connected to said trap/barrier, for expanding and/or retracting said trap/barrier; and
   iv. at least one particle removal aperture situated within said
   trap/barrier for removal of particles.

28. A method for preventing particles from escaping from a point of manipulation of a vessel or vessel-like structure comprising:
   a. inserting an angioplasty device into said vessel;
   b. positioning said device in said vessel;
   c. expanding said device;
   d. removing any particles resulting from said manipulation of said vessel through or to within said device;
   e. retracting said device; and
   f. removing said device from said vessel,
said device comprising:
   i. a catheter bundle for insertion into said vessel;
   ii. a trap/barrier connected to said catheter bundle;
   iii. expansion means, connected to said trap/barrier, for expanding and/or retracting said trap/barrier; and
   iv. at least one particle removal aperture situated within said trap/barrier for removal of particles.

* * * * *